United States Patent
Hu et al.

(10) Patent No.: US 12,356,980 B2
(45) Date of Patent: Jul. 15, 2025

(54) ANTI-LESION STORAGE METHOD AND STORAGE SYSTEM FOR CELLS, TISSUES OR ORGANS

(71) Applicant: Xi'an Bei Guang Medical Biotechnology Co., Ltd., Xi'an (CN)

(72) Inventors: Yifan Hu, Xi'an (CN); Peigeng Huang, Xi'an (CN)

(73) Assignee: XI'AN BEI GUANG MEDICAL BIOTECHNOLOGY CO., LTD., Shaanxi (CN)

( * ) Notice: Subject to any disclaimer, the term of this patent is extended or adjusted under 35 U.S.C. 154(b) by 31 days.

(21) Appl. No.: 17/945,816

(22) Filed: Sep. 15, 2022

(65) Prior Publication Data
US 2023/0329229 A1    Oct. 19, 2023

(30) Foreign Application Priority Data
Apr. 13, 2022    (CN) .......................... 202210386290.2

(51) Int. Cl.
A01N 1/122    (2025.01)
(52) U.S. Cl.
CPC ................................... A01N 1/122 (2025.01)
(58) Field of Classification Search
None
See application file for complete search history.

(56) References Cited

U.S. PATENT DOCUMENTS

2013/0143196 A1\*    6/2013    Joyner ............... A01N 1/0226
                                                                422/547

FOREIGN PATENT DOCUMENTS

| CN | 1698430 A | 11/2005 |
|----|-----------|---------|
| CN | 1784142 A | 6/2006 |
| CN | 103702557 A | 4/2014 |
| CN | 104054696 A | 9/2014 |
| CN | 104928235 A | 9/2015 |
| CN | 105593363 A | 5/2016 |
| CN | 107872954 A | 4/2018 |
| CN | 112218940 A | 1/2021 |
| CN | 114600872 A | 6/2022 |
| JP | H0623016 A | 2/1994 |
| JP | 2002525290 A | 8/2002 |
| JP | 2009528834 A | 8/2009 |
| JP | 2014510731 A | 5/2014 |
| JP | 2015174823 A | 10/2015 |
| JP | 2017518301 A | 7/2017 |
| JP | 2018520103 A | 7/2018 |
| WO | WO-8401292 A1 | 4/1984 |
| WO | WO-2012125955 A2 | 9/2012 |
| WO | WO-2016187353 A1 | 11/2016 |

OTHER PUBLICATIONS

Buchholz, D.H., Porten, J.H., Grode, G.A., Lin, A., Smith, J., Barber, T.A., Brda, J., & Kožar, I. (1985). Extended storage of single-donor platelet concentrate collected by a blood cell separator. Transfusion, 25. (Year: 1985).\*
Holme S, Heaton WA, Courtright M. Improved in vivo and in vitro viability of platelet concentrates stored for seven days in a platelet additive solution. Br J Haematol. Jun. 1987;66(2):233-8. doi: 10.1111/j.1365-2141.1987.tb01304.x. PMID: 3606958. (Year: 1987).\*
Buchholz, "Extended storage of single-donor platelet concentrate collected by a blood cell separator" Transfusion, 25. (Year: 1985), 6 pages.
Extended European Search Report for European Application No. EP22193656 mailed Jun. 16, 2023, 3 pages.
International Search Report for PCT Application No. PCT/CN2022/117855 dated Jan. 12, 2023, 6 pages.
Notice of Reasons for Refusal for Japanese Application No. JP2022145607 mailed Aug. 24, 2023, 14 pages.
Notice of Reasons for Refusal for Japanese Application No. JP2022145607 mailed Feb. 27, 2024, 4 pages.
Office Action for Chinese Application No. CN202210386290 mailed Jan. 12, 2023, 13 pages.
Office Action for Chinese Application No. CN202210386290 mailed Jul. 7, 2023, 12 pages.
Office Action for European Application No. 22193656.0 dated Jun. 28, 2023, 6 pages.
Reddoch, "Hemostatic Function of Apheresis Platelets Stored at 4° C. and 22° C.", vol. 41, pp. 54-61, 2014.
Shi et al., "Extended Storage of Platelets in a Novel Organ Preservation Solution, Somah", https://doi.org/10.1182/blood.V124.21.5110.5110 , Blood (2014) 124 (21): 5110, 3 pages.
Thatte et al., "Development and evaluation of a novel solution, Somah, for the procurement and preservation of beating and nonbeating donor hearts for transplantation," Circulation. Oct. 27, 2009; 120(17):1704-13. Epub Oct. 12, 2009.
Written Opinion for PCT Application No. PCT/CN2022/117855 dated Jan. 11, 2023, 7 pages.

\* cited by examiner

*Primary Examiner* — Allison M Fox
*Assistant Examiner* — Qinhua Gu
(74) *Attorney, Agent, or Firm* — COOLEY LLP

(57) ABSTRACT

The disclosure discloses an anti-lesion storage method and storage system for cells, tissues and organs, and relates to the technical field of storage of cells, tissues or organs. The method includes: adjusting a partial pressure of carbon dioxide in a suspension medium containing cells, tissues or organs to be stored to 30-50 mmHg. The inventors found that the regulation of the partial pressure of carbon dioxide in the suspension medium is advantageous for improving anti-lesions of cells, tissues or organs. In particular, the regulation of the partial pressure of carbon dioxide in the suspension medium can prolong the in vivo survival of platelets after transfusion of a platelet concentrate and protect the hemostatic function of platelets whiling effectively alleviating PSLs.

6 Claims, 6 Drawing Sheets

ANTI-LESION STORAGE METHOD AND STORAGE SYSTEM FOR CELLS, TISSUES OR ORGANS

CROSS-REFERENCE TO RELATED APPLICATIONS

The present application claims priority to Chinese patent application with the application number 2022103862902 filed to the China Patent Office on Apr. 13, 2022, entitled "Anti-lesion Storage Method and Storage System for Cells, Tissues or Organs", the entire contents of which are incorporated herein by reference.

TECHNICAL FIELD

The present disclosure relates to the technical field of storage of cells, tissues or organs, and particularly to an anti-lesion (anti-injury) storage method and storage system for cells, tissues and organs.

BACKGROUND ART

Platelets are cell debris formed by degranulation of megakaryocytes and have a major role in hemostasis. In clinical treatment, timely platelet transfusion can make more treatment time for patients, thereby improving prognosis and even saving lives. In recent years, the short supply of platelets has become the norm. There are many causes for the short supply of platelets, though one of the major factors is the excessively short storage life for conventional storage under continuous shaking in air at 22±2° C. (hereinafter, referred to simply as conventional storage). The storage life of platelets under such conditions is merely 5 days. In fact, the actual period for clinical use is merely about 3 days, apart from about 2 days required for collection, infectious disease screening and blood release. Platelets that are not used within this period must be scrapped. PNAS reported in 2017 that the expiration-caused scrap rate of platelets under conventional storage was as high as 10.3%. Such a high expiration-caused scrap rate not only results in huge economic losses (about 80 million US dollars per year in the United States), but also increases financial burden of patients, and furthermore, causes platelets already in short supply to be even more scarce. In addition, expiration-caused scrapping wastes precious blood resources and has a great impact on the enthusiasm of voluntary blood donors to donate blood, significantly reducing the probability that the blood donors donate blood again, which further intensifies the conflict between supply and demand of platelets from the source.

Numerous studies have shown that the major cause for the excessively short storage life of platelets under conventional storage is platelet storage lesions (PSLs). PSLs refer to a series of changes in cell membrane molecules, energy metabolism, survival time after transfusion, and hemostatic function in platelets during storage. Specific manifestation of PSLs includes expression of P-selectin (CD62P) and exposure of phosphatidylserine (PS) in cell membranes, shedding of GP Iba (CD42b), reduced production of adenosine triphosphate (ATP), which is an energy substance, along with rapid consumption of glucose and massive accumulation of lactic acid, as well as the consequent reduction in platelet aggregation rate and shortened survival time after transfusion. Therefore, the aim at prolonging the storage period of platelets by alleviating PSLs has always been a global research hotspot and a worldwide issue.

There is currently scant progress in blood storage methods to alleviate PSLs.

In view of this, the present disclosure is proposed.

SUMMARY

It is an object of the present disclosure to provide an anti-lesion storage method and storage method for cells, tissues and organs so as to prolong their storage life.

The present disclosure is realized as follows.

The present disclosure provides an anti-lesion storage method for cells, tissues or organs (ALSM-CTO), the method including: adjusting a partial pressure of carbon dioxide in a suspension medium containing cells, tissues or organs to be stored to 30-50 mmHg.

In an optional embodiment, the cells are selected from platelets.

In an optional embodiment, the cells are selected from platelet concentrate.

In an optional embodiment, a partial pressure of carbon dioxide in a suspension medium containing a platelet concentrate to be stored is increased to 30-50 mmHg.

The inventors found that the regulation of the partial pressure of carbon dioxide in the suspension medium is advantageous for improving anti-lesions of cells, tissues or organs.

In particular, the inventors found that regulating (e.g., increasing) the partial pressure of carbon dioxide in the suspension medium containing the platelet concentrate to be stored to 30-50 mmHg can effectively alleviate platelet CD62P expression, CD42b shedding, PS eversion, glucose consumption, lactic acid accumulation and reduction in ATP production, and also effectively alleviate aggregation impairment, reduction in a maximum amplitude (MA) value, and shortening of post-transfusion survival, and shorten bleeding time. Based on the above phenomena, it can be concluded that increasing the partial pressure of carbon dioxide in the suspension medium containing the platelet concentrate can effectively alleviate PSLs, prolong the post-transfusion survival of platelets, and protect the hemostatic function of platelets. Therefore, increasing the partial pressure of carbon dioxide in the suspension medium containing the platelet concentrate is advantageous for storage of platelet concentrate with a higher activity for a longer period of time.

Partial pressure of carbon dioxide ($PCO_2$) refers to the pressure generated by carbon dioxide molecules dissolved in a liquid, and is also known as carbon dioxide tension. The partial pressure of carbon dioxide can be measured by a blood gas analyzer.

The suspension medium for the platelet concentrate may be equivalently named as storage microenvironment and the like.

The platelet concentrate includes, but are not limited to, platelets donated for medical treatment or platelets artificially induced in vitro.

In a preferred embodiment of application of the present disclosure, the method includes: placing the platelet concentrate to be stored in a gas permeable container in a three-gas storage apparatus, and controlling a volume fraction of carbon dioxide in the three-gas storage apparatus to be 1-8%.

Preferably, the volume fraction of carbon dioxide in the three-gas storage apparatus is controlled to be 2-5%.

In a preferred embodiment of application of the present disclosure, the platelet concentrate to be stored is placed in the gas permeable container in the three-gas storage apparatus, and a volume fraction of oxygen in the three-gas storage apparatus is controlled to be 10-20%.

Preferably, the volume fraction of nitrogen in the three-gas storage apparatus is controlled to be 70-90%.

With the gas permeable material provided in the three-gas storage apparatus, an equilibrium between partial pressures of carbon dioxide inside and outside the gas permeable container can be maintained, thereby effectively alleviating PSLs, prolonging the post-transfusion survival of platelets, protecting the hemostatic function of platelets, and prolonging the storage life of platelets.

In a preferred embodiment of application of the present disclosure, the storage temperature in the three-gas storage apparatus is controlled to be 2-24° C., and the storage condition includes: standing storing when the storage temperature is 2-17° C., and keeping continuous shaking when the storage temperature is 18-24° C.

In an optional embodiment, one of, any combination of two, or a combination of all of three gases (volume fractions), namely carbon dioxide, oxygen and nitrogen, in the three-gas storage apparatus, is controlled.

The present disclosure also provides another storage method: placing the platelet concentrate to be stored in an air-tight container, and filling the air-tight container with any combination of two of, or a mixture of all of carbon dioxide, oxygen and nitrogen, with a volume fraction of carbon dioxide being 1-8%, a volume fraction of oxygen being 10-20%, and a volume fraction of nitrogen being 70-90%; and placing the air-tight container containing the platelet concentrate to be stored in the storage apparatus, controlling a storage temperature in the storage apparatus to be 2-24° C., and the storage condition includes: standing storing when the storage temperature is 2-17° C., and shaking storing when the storage temperature is 18-24° C.

With an air-tight container pre-filled with mixed gas provided in the storage apparatus, the partial pressure level of carbon dioxide in the air-tight container can also be maintained, thereby effectively alleviating PSLs, prolonging the post-transfusion survival of platelets, protecting the hemostatic function of platelets, and prolonging the storage life of platelets.

In an optional embodiment, a storage method for a platelet concentrate includes:

placing a platelet concentrate to be stored in a container equipped with a one-way gas valve or in a container made of a one-way gas permeable functional material, both of the containers allowing gas outside the container to enter without flowing out gas inside the container.

In an optional embodiment, the container having one-way gas permeable function and containing the platelet concentrate to be stored is placed in a storage apparatus, a storage temperature in the storage apparatus is controlled to be 2-24° C., and the platelet concentrate is allowed to keep standing when the temperature is 2-17° C., or kept shaking when the temperature is 18-24° C.

In an optional embodiment, a substance capable of producing carbon dioxide by a chemical reaction is added to the suspension medium for the platelet concentrate.

The substance capable of producing carbon dioxide by a chemical reaction is selected from at least one of carbonic acid, carbonates and enzymes; and it is, for example, a combination of carbonic acid and a carbonate, or a combination of carbonic acid, a carbonate and an enzyme.

The carbonate is selected from calcium carbonate or sodium bicarbonate. The enzyme includes, but is not limited to, hexokinase, phosphofructokinase-1, 3-phosphoglyceraldehyde dehydrogenase, phosphoglyceraldehyde kinase, pyruvate kinase, pyruvate dehydrogenase complex, isocitrate dehydrogenase, α-ketoglutarate dehydrogenase complex, succinyl-CoA synthase, succinate dehydrogenase, malate dehydrogenase, fatty acyl-CoA synthase, L-3-hydroxy-4-trimethylammonium butyric acid, carnitine acyltransferase I, carnitine acyltransferase II, β-ketoacyl-CoA thiolase, fatty acyl-CoA dehydrogenase, enoyl-CoA hydratase, or β-hydroketothiolase of β-hydroxy fatty acyl-CoA dehydrogenase.

In a preferred embodiment of application of the present disclosure, sodium bicarbonate, which can generate carbon dioxide, is added to the platelet concentrate to be stored in advance, then the platelet concentrate is charged in a container equipped with a one-way gas valve, the container is placed in a storage apparatus, a storage temperature in the storage apparatus is controlled to be 2-24° C., and the platelet concentrate is allowed to keep standing when the temperature is 2-17° C., or kept shaking when the temperature is 18-24° C.

In a preferred embodiment of application of the present disclosure, a platelet collection device containing the platelets to be stored is pre-filled with any combination of two of, or a mixture of all of carbon dioxide, oxygen and nitrogen, with a volume fraction of carbon dioxide being 1-8%, a volume fraction of oxygen being 10-20%, and a volume fraction of nitrogen being 70-90%.

In an optional embodiment, the partial pressure of carbon dioxide in the suspension medium for the platelet concentrate is controlled to 30-50 mmHg during the collection of the platelets to be stored.

In a preferred embodiment of application of the present disclosure, the collection device for the platelets to be stored is prefilled with a substance capable of producing carbon dioxide by a chemical reaction.

In an optional embodiment, the substance capable of producing carbon dioxide by a chemical reaction is selected from at least one of carbonic acid, carbonates or enzymes.

In an optional embodiment, the carbonate is selected from calcium carbonate or sodium bicarbonate, and the enzyme is selected from hexokinase, phosphofructokinase-1, 3-phosphoglyceraldehyde dehydrogenase, phosphoglyceraldehyde kinase, pyruvate kinase, pyruvate dehydrogenase complex, isocitrate dehydrogenase, α-ketoglutarate dehydrogenase complex, succinyl-CoA synthase, succinate dehydrogenase, malate dehydrogenase, fatty acyl-CoA synthase, L-3-hydroxy-4-trimethylammonium butyric acid, carnitine acyltransferase I, carnitine acyltransferase II, β-ketoacyl-CoA thiolase, fatty acyl-CoA dehydrogenase, enoyl-CoA hydratase, or β-ketothiolase of β-hydroxy fatty acyl-CoA dehydrogenase.

In a preferred embodiment of application of the present disclosure, an organism of the platelet concentrate to be stored is selected from human, monkey, sheep, rabbit, mouse, swine, dog, cat, horse, or cow.

The present disclosure also provides a storage system for cells, tissues or organs, which can control a partial pressure of carbon dioxide in a suspension medium containing the cells, tissues or organs to be stored to be 30-50 mmHg. The storage system for cells, tissues or organs includes a one-way gas permeable container for storing the cells, tissues or organs, a carbon dioxide-releasing substance, and a storage apparatus. The carbon dioxide-releasing substance is selected from at least one of carbonic acid, carbonates, or enzymes.

In a preferred embodiment of application of the present disclosure, the cells are selected from platelets; and in a preferred embodiment of application of the present disclosure, the cells are selected from platelet concentrate.

In a preferred embodiment of application of the present disclosure, the one-way gas permeable container is a container equipped with a one-way gas valve, and the carbon dioxide-releasing substance is selected from sodium bicarbonate.

The platelet concentrate with sodium bicarbonate added therein is charged in the container equipped with a one-way gas valve, then the container is placed in a storage apparatus, a storage temperature in the storage apparatus is controlled to be 2-24° C., and the platelet concentrate is allowed to keep standing when the temperature is 2-17° C., or kept shaking when the temperature is 18-24° C.

Replacement of a conventional gas permeable container with a container with a one-way gas permeable function not only facilitates entry of oxygen required for platelet metabolism, but also prevents leakage of $CO_2$ produced during the metabolic process. In addition, lactic acid generated by platelet metabolism can chemically react with the added sodium bicarbonate to produced carbon dioxide. As such, the partial pressure of carbon dioxide can be further increased while consuming lactic acid that is detrimental to platelet storage, thereby effectively alleviating PSLs, prolonging the post-transfusion survival of platelets, protecting the hemostatic function of platelets, and prolonging the storage life of platelets.

The present disclosure has the following advantageous effects.

The present disclosure provides an anti-lesion storage method for cells, tissues and organs. Controlling the partial pressure of carbon dioxide in the suspension medium containing the cells, tissues and organs to be stored to 30-50 mmHg can effectively alleviate CD62P expression, CD42b shedding, PS eversion, glucose consumption, lactic acid accumulation and reduction in ATP production, and alleviate aggregation impairment, reduction in the MA value, and shortening of post-transfusion survival. Therefore, increasing the partial pressure of carbon dioxide in the suspension medium is advantageous for storage of platelets with a higher activity for a longer period of time.

In addition, the present disclosure provides a storage system for cells, tissues or organs.

BRIEF DESCRIPTION OF THE DRAWINGS

In order to illustrate the technical solutions of the examples of the present disclosure more clearly, the accompanying drawings used for the examples will be briefly introduced. It should be appreciated that the following drawings show some examples of the present disclosure only, and thus should not be construed as a limitation of the scope. For those of ordinary skill in the art, other related drawings can also be obtained according to these drawings without any creative effort.

DETAILED DESCRIPTION OF THE EMBODIMENTS

Figure 1A:
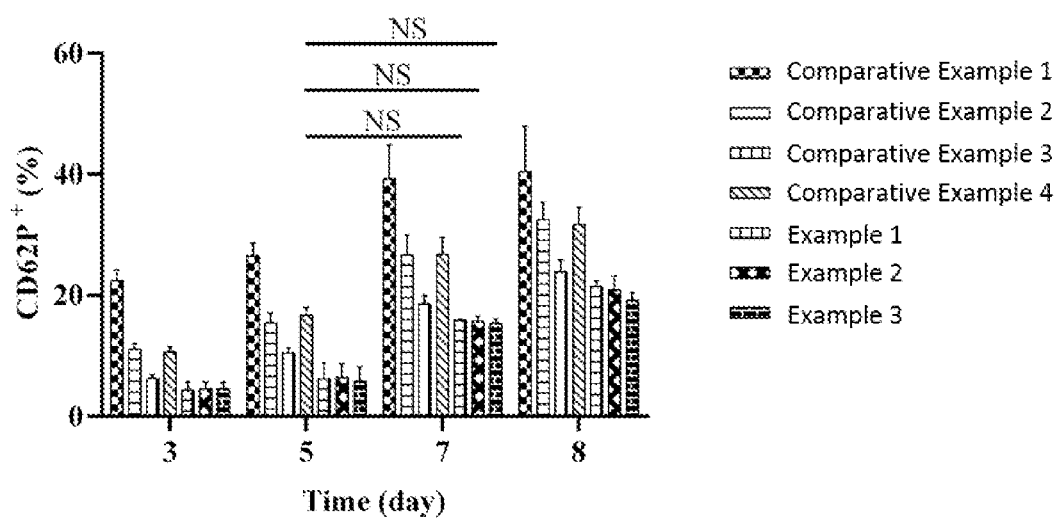
FIG. 1A shows statistical data of CD62P expression of the platelets stored in Examples and Comparative Examples.

To make the objects, technical solutions, and advantages of the examples of the present disclosure more clear, the technical solutions in the examples of the present disclosure will be described clearly and completely below. If the specific conditions are not indicated in the examples, the examples are carried out according to the conventional conditions or the conditions recommended by the manufacturers. The used reagents or instruments without indication of the manufacturer are conventional products that can be purchased from the market.

The features and performances of the present disclosure will be described in further detail below in conjunction with the examples.

Main reagents and materials in this example include:

Anti-human CD62P-FITC antibody; Annexin V-FITC apoptosis detection kit available from BD Company, USA; Anti-human CD42b-PE, Anti-human CD41-FITC and Anti-mouse CD41-APC available from Biolegend Company, USA; arachidonic acid (AA) detection kit for platelet aggregation function and adenosine diphosphate (ADP) detection kit for platelet aggregation function available from Sysmex Corporation, Japan; ATP detection kit available from Shanghai Beyotime Biotechnology Co., Ltd.; Amicus Separator, a platelet separator, and attached platelet storage bag (Amicus, USA), 3131 three-gas incubator (Thermo, USA), SYNERGY microplate reader (Bio-Tex, USA), FACS Canto flow cytometer (BD, USA), GEM3500 blood gas analyzer (IL, USA), CS-2400 automated blood coagulation analyzer (Sysmex, Japan), 5000 thromboelastography analyzer (Haemoscope, USA), and non-obese diabetes server combined immune-deficiency (NOD SCID) mice available from Cyagen Biosciences Inc.

Example 1

This example provides a platelet storage method including: controlling a partial pressure of carbon dioxide in a suspension medium for a platelet concentrate to be stored to be 40 mmHg.

Specifically, the platelet concentrate to be stored was first prepared as follows. A healthy adult who had not taken any medicament within the past 10 days was recruited as a volunteer and allowed to sign the informed consent form. General examinations were conducted on the blood donor in accordance with the requirement of health examinations for blood donors. After passing the examinations, the volunteer was guided for the blood collection, and 20 U of fresh platelets were directly collected from the volunteer using a blood cell separator. The collected platelets were stored under shaking at 22±2° C. for later use.

The above platelets were charged in a gas permeable platelet storage bag, then placed in a three-gas incubator, and stored under shaking at 22±2° C.

The gas composition in the three-gas incubator was controlled to be 3.5% $CO_2$, 17% $O_2$, and 80% $N_2$.

Example 2

The present example provides a platelet storage method including: charging a platelet concentrate to be stored in an air-tight container, filling the container with a mixed gas including 3.5% carbon dioxide, 17% oxygen, and 80% nitrogen, all in volume fractions, then placing the container in a storage apparatus, and storing it under shaking at 22±2° C. The remaining steps were the same as in Example 1.

Example 3

The present example provides a platelet storage method including: charging a platelet concentrate to be stored in a container equipped with a one-way gas valve that only allows entry of gas outside, and charging sodium bicarbonate in the container in advance, then placing the container in a storage apparatus, and storing it under shaking at 22±2° C. The remaining steps were the same as in Example 1.

Comparative Example 1

The only difference from Example 1 is that the partial pressure of carbon dioxide in the suspension medium for the platelet concentrate to be stored was controlled to be 5 mmHg.

Comparative Example 2

The only difference from Example 1 is that the partial pressure of carbon dioxide in the suspension medium for the platelet concentrate to be stored was controlled to be 30 mmHg.

Comparative Example 3

The only difference from Example 1 is that the partial pressure of carbon dioxide of the suspension medium of the platelet concentrate to be stored was controlled to be 50 mmHg.

Comparative Example 4

The only difference from Example 1 is that the platelet concentrate to be stored was charged in a traditional gas permeable platelet storage bag, then placed in a shaking storage apparatus for platelets, and stored under shaking at 22±2° C.

Experimental Example 1

The platelets of the above-mentioned Examples and Comparative Examples were analyzed for CD62P expression, PS eversion, and D42b shedding. Experiment grouping and respective treatments were performed as follows. The platelets to be used were equally divided into 7 groups, and these groups were stored according to the methods of Example 1, Example 2, Example 3, Comparative Example 1, Comparative Example 2, Comparative Example 3, and Comparative Example 4, respectively. Then, an appropriate amount of each of samples to be tested was taken on the 3rd, 5th, 7th and 8th days of storage, and marking for CD62P, PS, and CD42b was conducted with reference to the instructions of Anti-CD62P-FITC antibody, Annexin V-FITC apoptosis detection kit, and Anti-CD42b-PE antibody, respectively, followed by flow cytometry.

Figure 1B:
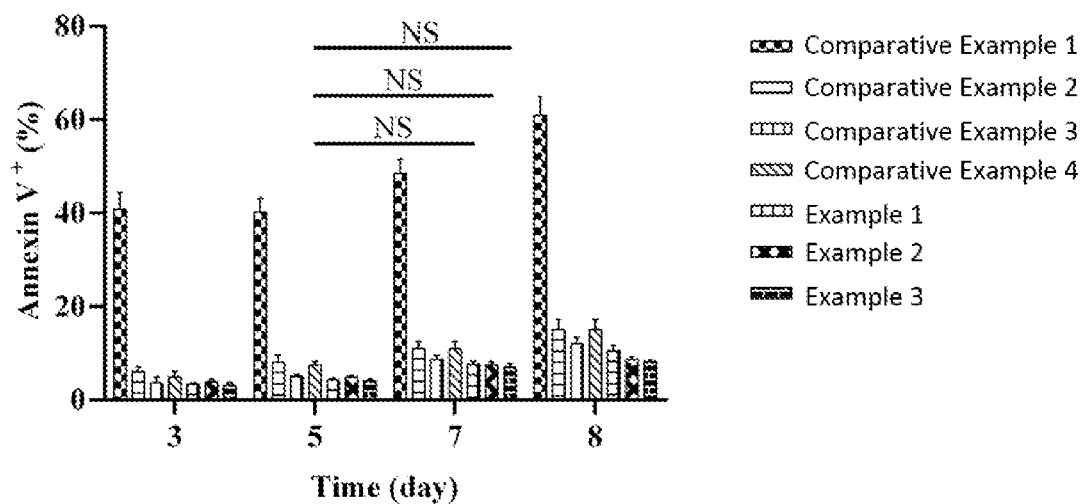
FIG. 1B shows statistical data of PS eversion of the platelets stored in Examples and Comparative Examples.
Figure 1C:
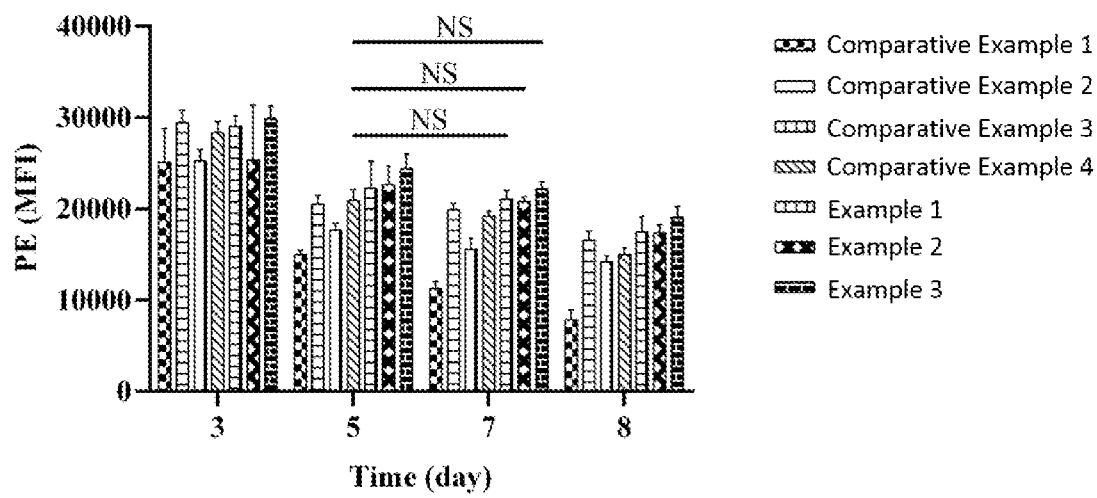
FIG. 1C shows statistical data of CD42b shedding of the platelets stored in Examples and Comparative Examples.

FIG. 1A, FIG. 1B, and FIG. 1C show the statistical analysis of CD62P expression, PS eversion, and CD42b shedding in the respective groups on the 3rd, 5th, 7th and 8th days of storage. It can be found that, from the results of Examples 1 and 4 comparative examples, with the increase of $CO_2$ partial pressure in the suspension medium for the platelet concentrate, both the CD62P-positive platelet ratio representing CD62P expression and Annexin V-positive platelet ratio representing PS eversion first decreased and then increased, while the mean fluorescence intensity of PE representing CD42b shedding first increased and then decreased. In the method of Example 1, the CD62P-positive platelet ratio and Annexin V-positive platelet ratio were the lowest, and the mean fluorescence intensity was the highest. The CD62P-positive platelet ratio and Annexin V-positive platelet ratio in Example 1, Example 2, and Example 3 decreased, and the mean fluorescence intensity of PE increased, compared with Comparative Example 4, for the same storage duration. The CD62P-positive platelet ratio, Annexin V-positive platelet ratio, and the mean fluorescence intensity of PE in Example 1, Example 2, and Example 3 on the 7th day of storage were not statistically different from those of Comparative Example 4 on the 5th day of storage. CD62P expression, PS eversion, and CD42b shedding were found when PSLs occurred. Therefore, the above results indicate that the partial pressure of $CO_2$ in the suspension medium for the platelet concentrate to be stored is associated with the occurrence of PSLs. The methods used in Example 1, Example 2, and Example 3 all increase the $CO_2$ partial pressure in the suspension medium for the platelet concentrate to be stored to 40 mmHg, thereby delaying the occurrence of PSLs. In addition, it is also suggested that the methods used in Example 1, Example 2, and Example 3 can extend the in vitro storage life of platelets from 5 days in a conventional method to 7 days while improving the in vitro storage effect of platelets.

Experimental Example 2

The blood gas analysis was performed on the platelet groups of the above-mentioned Examples and Comparative Examples. The only difference from Experimental Example 1 was that the blood gas analysis was performed with reference to the instructions of the blood gas analyzer, and the ATP concentration analysis was performed with reference to the instructions of the ATP detection kit.

Figure 2A:
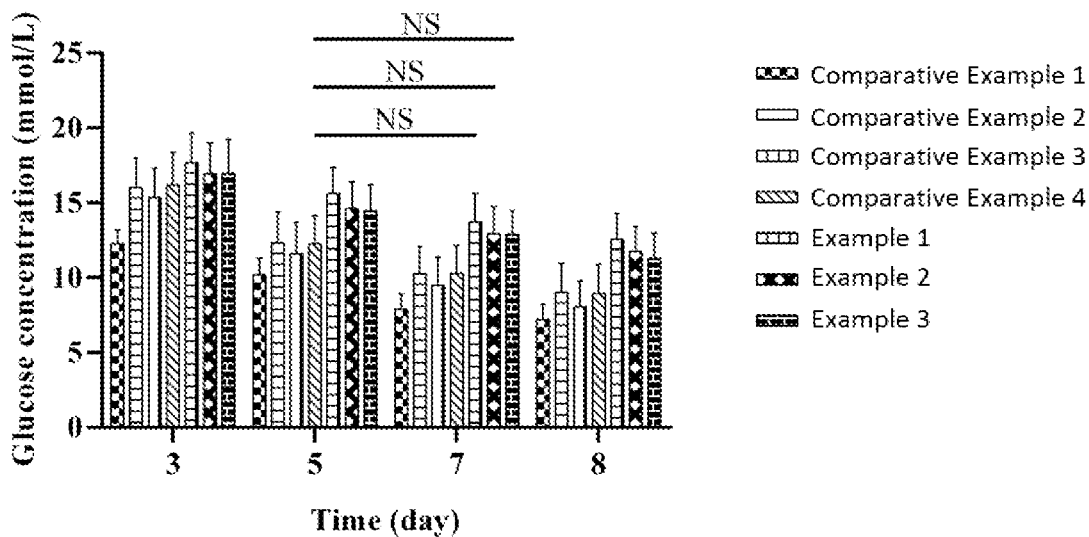
FIG. 2A shows statistical data of glucose consumption of the platelets stored in Examples and Comparative Examples.
Figure 2B:
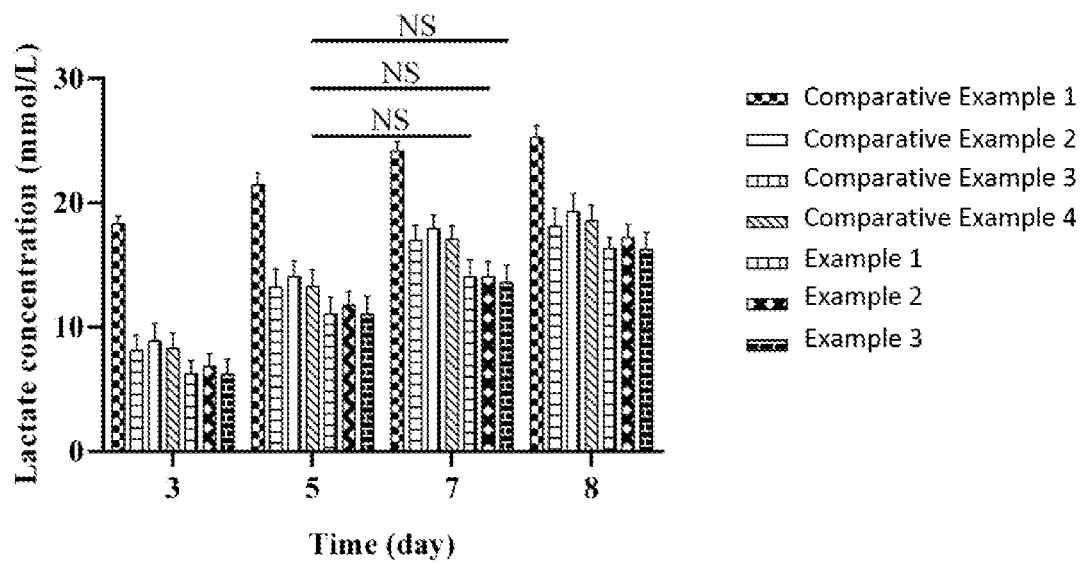
FIG. 2B shows statistical data of lactic acid production of the platelets stored in Examples and Comparative Examples.
Figure 2C:
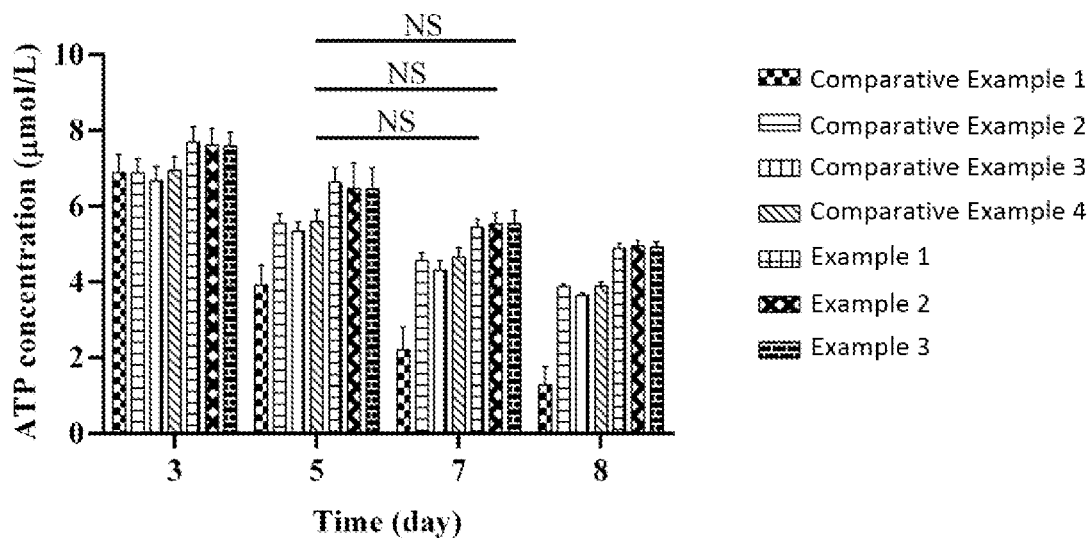
FIG. 2C shows statistical data of ATP concentration of the platelets stored in Examples and Comparative Examples.

FIG. 2A, FIG. 2B, and FIG. 2C show the statistical analysis of glucose consumption, lactic acid production, and ATP concentration of the respective groups on the 3rd, 5th, 7th and 8th days of storage. It can be found that, from the results of Examples 1 and 4 comparative examples, with the increase of $CO_2$ partial pressure in the suspension medium for the platelet concentrate, both glucose consumption and lactic acid production first decreased and then increased, and ATP concentration first increased and then decreased. In the method of Example 1, the glucose consumption and lactic acid production were the lowest, and ATP concentration was the highest. The glucose consumption and lactic acid production in Example 1, Example 2, and Example 3 all decreased, and the ATP concentration was increased, compared with Comparative Example 4, for the same storage duration. The glucose consumption, lactic acid production and ATP concentration in Example 1, Example 2, and Example 3 on the 7th day of storage were not statistically different from those of Comparative Example 4 on the 5th day of storage. ATP production was also reduced when PSLs occurred, which was accompanied by rapid glucose consumption and massive accumulation of lactic acid. Therefore, the above results further indicate that the partial pressure of $CO_2$ in the suspension medium for the platelet concentrate to be stored is associated with the occurrence of PSLs. The methods used in Example 1, Example 2, and Example 3 all increase the $CO_2$ partial pressure in the suspension medium for the platelet concentrate to be stored to 40 mmHg, thereby delaying the occurrence of PSLs. In addition, it is further suggested that the methods used in Example 1, Example 2, and Example 3 can extend the in vitro storage life of platelets from 5 days in a conventional method to 7 days while improving the in vitro storage effect of platelets.

Experimental Example 3

The platelets stored in Example 1 and Comparative Example 4 above were detected for their aggregation function. An appropriate amount of each of samples to be tested was taken on the 3rd, 5th and 7th days of storage. The platelet aggregation function thereof was detected using an automated blood coagulation analyzer in reference to the instructions of AA detection kit for platelet aggregation function (turbidimetric method) and ADP detection kit for platelet aggregation function (turbidimetric method).

Figure 3A:
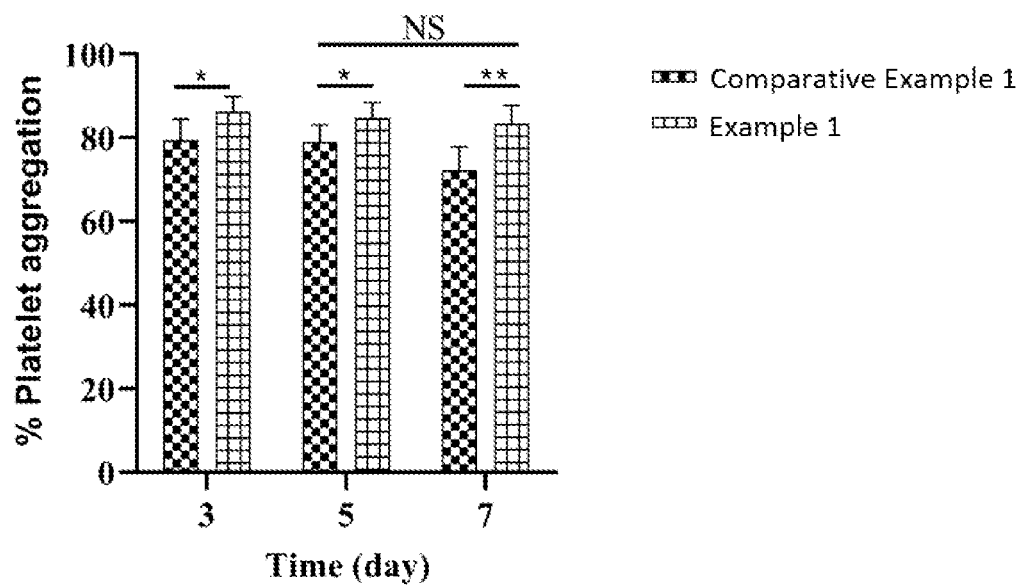
FIG. 3A shows statistical data of aggregation function of the platelets stored in Example 1 and Comparative Example 4 using AA as an inducer.
Figure 3B:
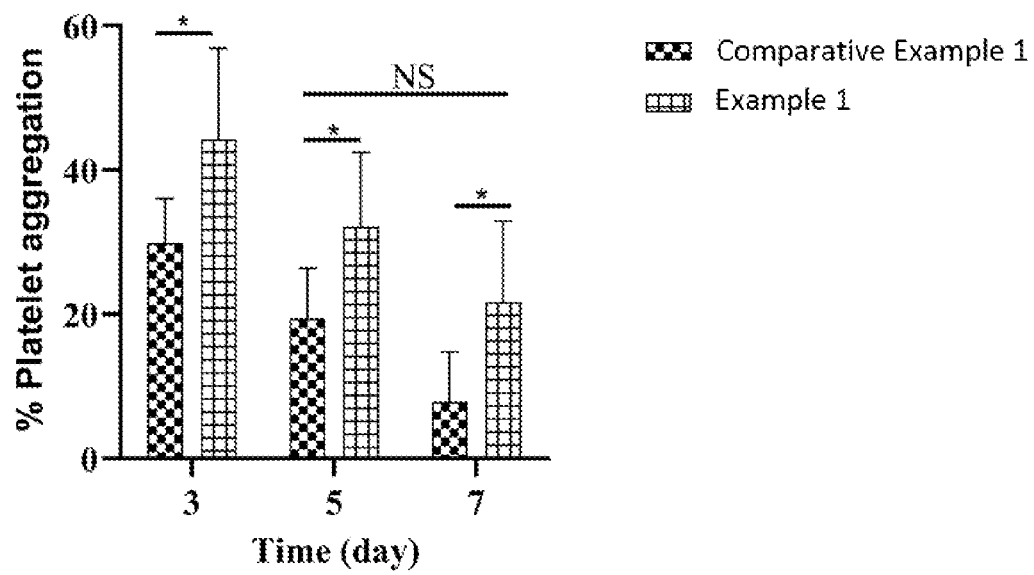
FIG. 3B shows statistical data of aggregation function of platelets stored in Example 1 and Comparative Example 4 using ADP as an inducer.

FIG. 3A and FIG. 3B show the statistical analysis of the two platelet aggregation tests using AA or ADP as inducers, respectively. The results showed that AA-induced or ADP-induced platelets stored in both Example 1 and Comparative Example 4 had reduced aggregation rates over time. The platelets stored in Example 1 had increased aggregation rate compared with Comparative Example 4, for the same storage duration. In addition, the aggregation rate of the platelets stored in Example 1 on the 7th day of storage was not statistically different from that of the platelets stored in Comparative Example 4 on the 5th day of storage. The aggregation rate of platelets is proportional to the hemostatic function of platelets. Therefore, these results indicate that increasing the $CO_2$ partial pressure in the suspension medium for in vitro storage of the platelet concentrate to 40 mmHg can protect the hemostatic function of platelets, further suggesting that increasing the $CO_2$ partial pressure in the suspension medium for in vitro storage of the platelet concentrate to 40 mmHg not only improves the in vitro storage effect of platelets, but also extends the in vitro storage life of platelets from 5 days in a conventional method to 7 days.

Experimental Example 4

MA values of the platelets stored in Example 1 and Comparative Example 1 above were detected. A healthy adult who had not taken any medicament within the past 10 days was recruited as a volunteer. After disinfection, 3 mL of peripheral blood was collected from median cubital vein and charged in a test tube containing 3.8% sodium citrate anticoagulant, centrifuged at 100 g for 10 minutes to separate platelet-rich plasma and cells in the lower layer, and then centrifuged at 2000 g for 10 minutes to separate the platelets and plasma in the platelet-rich plasma. Then, the obtained plasma was mixed with the cells in the lower layer obtained before to obtain platelet-deficient human peripheral blood. Subsequently, the human platelets stored in Example 1 and Comparative Example 1 were each added to the platelet-deficient human peripheral blood to give a final concentration of 200×109/L. After mixing thoroughly, the MA value was detected in reference to the instructions of the kit.

Figure 4:
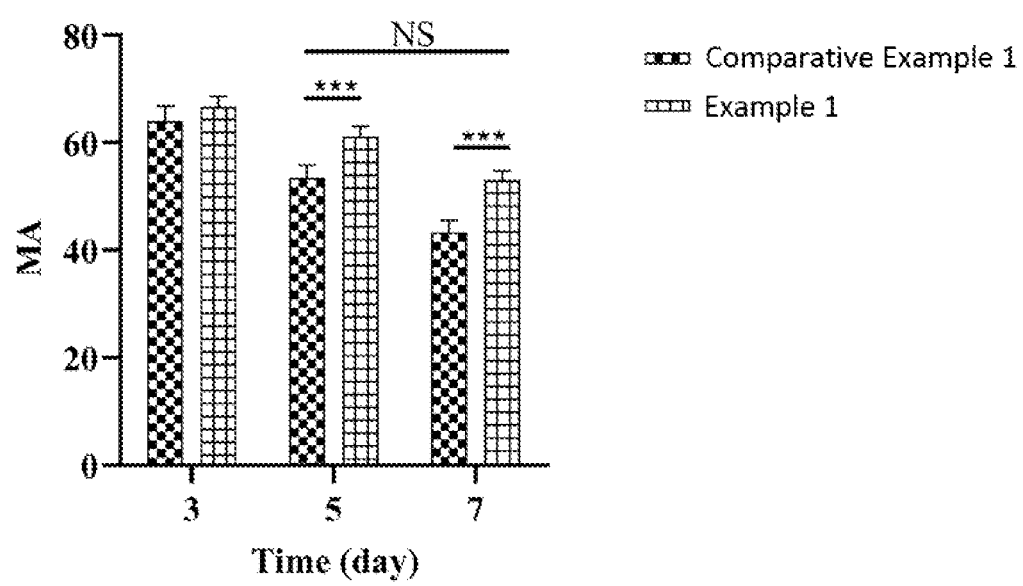
FIG. 4 shows statistical data of MA values of the platelets stored in Example 1 and Comparative Example 4.

FIG. 4 shows the statistical analysis of the MA values of the two groups on the 5th and 7th day. The results found that the MA value of Example 1 was higher than that of Comparative Example 1, for the same storage duration. In addition, there was no statistical difference between Example 1 on the 7th day of storage and Comparative Example 1 on the 5th day of storage. The MA value is one of the classic indicators that comprehensively reflect hemostatic function of platelets, and is proportional to hemostatic function of platelets. This result further confirms that increasing the $CO_2$ partial pressure in the suspension medium for in vitro storage of the platelet concentrate to 40 mmHg can protect the hemostatic function of platelets, further suggesting that increasing the $CO_2$ partial pressure in the suspension medium for in vitro storage of the platelet concentrate to 40 mmHg can extend the in vitro storage life of platelets from 5 days in a conventional method to 7 days.

Experimental Example 5

In this experimental example, the platelets stored in Example 1 and Comparative Example 1 above were subjected to analysis and statistics of the post-transfusion survival. An appropriate amount of each of samples to be tested were taken on the 3rd, 5th and 7th days of storage, and then transfused into mice through the tail vein. Then, an appropriate amount of peripheral blood was collected from the tip of the tail 12 hours after transfusion. The peripheral blood after lysis of red blood cells were co-labeled with Anti-human CD41-FITC and Anti-mouse CD41-APC. The ratio of FITC+/APC+ was analyzed by flow cytometry.

Figure 5:
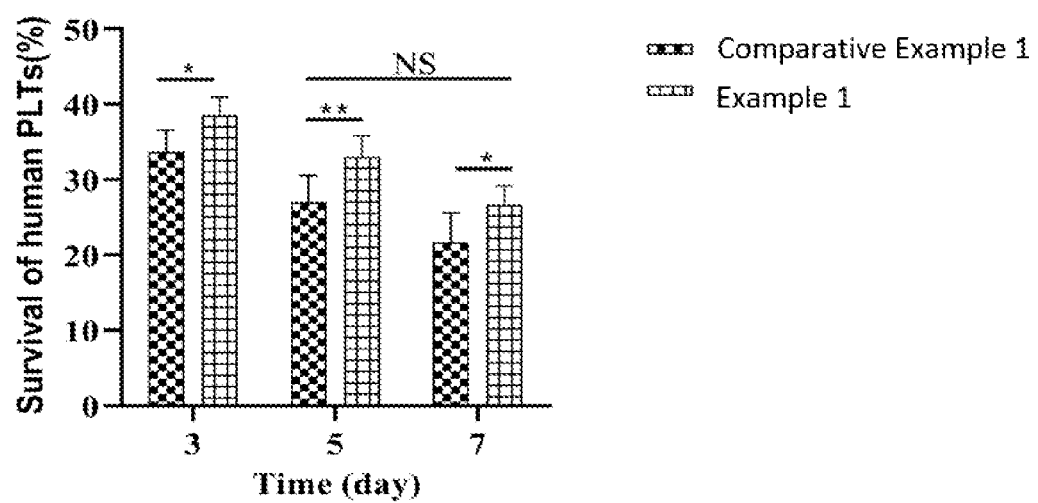
FIG. 5 shows statistical data of post-transfusion survival of platelets stored in Example 1 and Comparative Example 4.

FIG. 5 shows the statistical data of post-transfusion survival of the two groups of platelets. The results showed that, the ratio of FITC+/APC+ of the platelets stored in Example 1 and Comparative Example 1 both decreased after transfusion over time after transfusion, and the ratios of FITC+/APC+ of Example 1 after transfusion were all higher than those of Comparative Example 1, for the same storage duration. In addition, there was no statistical difference between Example 1 on the 7th day of storage and Comparative Example 1 on the 5th day of storage. This result shows that increasing the $CO_2$ partial pressure in the suspension medium for in vitro storage of the platelet concentrate to 40 mmHg can extend the post-transfusion survival of platelet, and also indicates that increasing the $CO_2$ partial pressure in the suspension medium for the platelet concentrate to 40 mmHg can extend the in vitro storage life of platelets from 5 days in a conventional method to 7 days.

It is well known to those skilled in the art that PSLs would occur in platelets during in vitro storage. Specific manifestation of PSLs includes CD62P expression, CD42b shedding, PS eversion, glucose consumption, lactic acid accumulation, and reduction in ATP production occurred in platelets, along with impaired hemostatic function, shortened post-transfusion survival, and so on. A series of studies made by the inventors found that increasing the partial pressure of $CO_2$ in the storage medium to 40 mmHg can effectively alleviate activation, apoptosis, and CD42b shedding of platelets stored. Furthermore, after the partial pressure of $CO_2$ in the storage medium to 40 mmHg, the hemostatic function was also greatly improved, and the post-transfusion survival was significantly prolonged.

In conclusion, the technical solution disclosed in the present disclosure is a new strategy for enhancing storage effect for platelets and prolonging their storage life by improving the in vitro storage conditions for platelets, and is of great significance for the storage of platelets.

The above descriptions are only preferred examples of the present disclosure, and are not intended to limit the present disclosure. For those skilled in the art, various modifications and changes can be made to the present disclosure. Any modification, equivalent replacement, improvement, and the like made within the spirit and principle of the present disclosure shall be included within the protective scope of the present disclosure.

What is claimed is:

1. An anti-lesion storage method for cells comprising:
adjusting a partial pressure of carbon dioxide in a suspension medium containing cells, the cells comprising platelets or a platelet concentrate, with 30 mmHg or 50 mmHg;
placing the platelets or the platelet concentrate in a collection device; and
placing the collection device in a three-gas storage apparatus,
wherein:
a volume fraction of carbon dioxide in the three-gas storage apparatus is controlled to be 3.5%,
a volume fraction of oxygen in the three-gas storage apparatus is controlled to be 17%,
a storage condition in the three-gas storage apparatus is controlled to a temperature between 2-24° C., such that, when the temperature is between 2-17° C., the storage condition corresponds to a standing storage condition, and when the temperature is between 18-24° C., the storage condition corresponds to a shaking storage condition.

2. The method according to claim 1, wherein:
a substance capable of producing carbon dioxide by a chemical reaction is added to the suspension medium,
the substance comprises at least one of carbonic acid, a carbonate, and an enzyme,
the carbonate comprises calcium carbonate or sodium bicarbonate, and
the enzyme comprises hexokinase, phosphofructokinase-1, 3-phosphoglyceraldehyde dehydrogenase, phosphoglyceraldehyde kinase, pyruvate kinase, pyruvate dehydrogenase complex, isocitrate dehydrogenase, α-ketoglutarate dehydrogenase complex, succinyl-CoA synthase, succinate dehydrogenase, malate dehydrogenase, fatty acyl-CoA synthase, L-3-hydroxy-4-trimethylammonium butyric acid, carnitine acyltransferase I, carnitine acyltransferase II, β-ketoacyl-CoA thiolase, fatty acyl-CoA dehydrogenase, enoyl-CoA hydratase, or β-hydroketothiolase of β-hydroxy fatty acyl-CoA dehydrogenase.

3. The method according to claim 1, wherein:
the collection device for the platelets to be stored is pre-filled with a substance capable of producing carbon dioxide by a chemical reaction, the substance comprising at least one of carbonic acid, a carbonate or an enzyme;
the carbonate comprises calcium carbonate or sodium bicarbonate,
the enzyme comprises hexokinase, phosphofructokinase-1, 3-phosphoglyceraldehyde dehydrogenase, phosphoglyceraldehyde kinase, pyruvate kinase, pyruvate dehydrogenase complex, isocitrate dehydrogenase, α-ketoglutarate dehydrogenase complex, succinyl-CoA synthase, succinate dehydrogenase, malate dehydrogenase, fatty acyl-CoA synthase, L-3-hydroxy-4-trimethylammonium butyric acid, carnitine acyltransferase I, carnitine acyltransferase II, β-ketoacyl-CoA thiolase, fatty acyl-CoA dehydrogenase, enoyl-CoA hydratase, or β-ketothiolase of β-hydroxy fatty acyl-CoA dehydrogenase; and
the platelets or the platelet concentrate correspond to platelets or platelet concentrate from human, monkey, sheep, rabbit, mouse, swine, dog, cat, horse, or cow organism.

4. A storage system for cells,
wherein:
the system is configured for controlling a partial pressure of carbon dioxide in a suspension medium containing the cells, and
the cells are stored at a pressure with 30 mmHg or 50 mmHg;
the system comprises:
a one-way collection device for receiving the cells, a carbon dioxide-releasing substance, and
a three-gas storage apparatus;
and wherein:
the carbon dioxide-releasing substance comprises at least one of carbonic acid, a carbonate, and an enzyme;
the cells are platelets or platelet concentrate, and the platelets or platelet concentrate is placed in the collection device;
upon placing the platelets or platelet concentrate in the one-way collection device, and placing the one-way collection device in the three-gas storage apparatus, the system is configured to control:
a volume fraction of carbon dioxide in the three-gas storage apparatus to 3.5%,
a volume fraction of oxygen in the three-gas storage apparatus to 17%,
and
a storage condition in the three-gas storage apparatus is controlled to a temperature between 2-24° C., such that, when the temperature is between 2-17° C., the storage condition corresponds to a standing storage condition, and when the temperature is between 18-24° C., the storage condition corresponds to a shaking storage condition.

5. An anti-lesion storage method for cells comprising:
adjusting a partial pressure of carbon dioxide for a suspension medium containing cells, wherein the cells comprise platelets or a platelet concentrate and the partial pressure is 30 mmHg or 50 mmHg;
placing the platelets or the platelet concentrate in a container equipped with a one-way gas valve or in a container made of a one-way gas permeable functional material;
placing the container in a storage apparatus; and
controlling a storage temperature in the storage apparatus to between 2-24° C.,
wherein upon the storage temperature being between 2-17° C., the platelets or the platelet concentrate is not shaken, and upon the storage temperature being between 18-24° C., the platelets or the platelet concentrate is shaken.

6. An anti-lesion storage method for cells comprising:
adjusting a partial pressure of carbon dioxide for a suspension medium containing cells, wherein the cells comprise platelets or a platelet concentrate and the partial pressure is 30 mmHg or 50 mmHg;

placing the platelets or the platelet concentrate in an air-tight container;

filling the air-tight container with a mixture of carbon dioxide, oxygen and nitrogen, wherein volume fractions of carbon dioxide and oxygen are 3.5% and 17%, respectively;

placing the air-tight container in a storage apparatus for storing therein; and controlling a storage temperature in the storage apparatus, wherein, the storage temperature comprises:
- a standing storage condition when the storage temperature is between 2-17° C., and
- a shaking storage condition when the storage temperature is between 18-24° C.

* * * * *